(12) United States Patent
Hau-Riege

(10) Patent No.: US 7,212,282 B2
(45) Date of Patent: May 1, 2007

(54) METHOD FOR CHARACTERIZING MASK DEFECTS USING IMAGE RECONSTRUCTION FROM X-RAY DIFFRACTION PATTERNS

(75) Inventor: Stefan Peter Hau-Riege, Fremont, CA (US)

(73) Assignee: The Regents of the University of California, Oakland, CA (US)

( * ) Notice: Subject to any disclaimer, the term of this patent is extended or adjusted under 35 U.S.C. 154(b) by 332 days.

(21) Appl. No.: 10/783,520

(22) Filed: Feb. 20, 2004

(65) Prior Publication Data

US 2005/0185173 A1 Aug. 25, 2005

(51) Int. Cl.
*G01N 21/00* (2006.01)
*G03F 1/00* (2006.01)
*G06K 9/00* (2006.01)

(52) U.S. Cl. .............................. 356/237.5; 356/237.1; 430/5; 382/145

(58) Field of Classification Search .. 356/237.1–237.6, 356/394; 250/559.44, 492.21, 492.22, 307, 250/310; 382/144–145; 430/5
See application file for complete search history.

(56) References Cited

U.S. PATENT DOCUMENTS

| | | | | |
|---|---|---|---|---|
| 4,751,169 A * | 6/1988 | Behringer et al. | ........... | 430/296 |
| 5,230,970 A * | 7/1993 | Atwood et al. | ................. | 430/5 |
| 6,016,357 A * | 1/2000 | Neary et al. | ................. | 382/144 |
| 6,091,846 A * | 7/2000 | Lin et al. | .................... | 382/145 |
| 6,322,935 B1 * | 11/2001 | Smith | ............................. | 430/5 |
| 6,335,129 B1 * | 1/2002 | Asano et al. | ................... | 430/5 |
| 6,340,543 B1 * | 1/2002 | Nagamura et al. | ............. | 430/5 |
| 6,438,438 B1 * | 8/2002 | Takagi et al. | ............... | 700/121 |
| 6,684,164 B1 * | 1/2004 | Chen et al. | .................. | 702/35 |
| 6,801,650 B1 * | 10/2004 | Kikuchi et al. | ............. | 382/145 |
| 6,864,971 B2 * | 3/2005 | Lin et al. | .................. | 356/237.4 |
| 6,967,168 B2 * | 11/2005 | Stearns et al. | ............. | 438/706 |

OTHER PUBLICATIONS

"Image reconstruction from electron and X-ray diffraction patterns using iterative algorithms: experiment and simulation," Ultramicroscopy, vol. 90, Issues 2-3, Feb. 2002, pp. 171-195.
"Phase retrieval algorithms: a comparison," Applied Optics, vol. 21, No. 15, Aug. 1, 1982, pp. 2758-2769.

* cited by examiner

*Primary Examiner*—Sang H. Nguyen
(74) *Attorney, Agent, or Firm*—John P. Wooldridge; John H. Lee

(57) ABSTRACT

The invention applies techniques for image reconstruction from X-ray diffraction patterns on the three-dimensional imaging of defects in EUVL multilayer films. The reconstructed image gives information about the out-of-plane position and the diffraction strength of the defect. The positional information can be used to select the correct defect repair technique. This invention enables the fabrication of defect-free (since repaired) X-ray Mo—Si multilayer mirrors. Repairing Mo—Si multilayer-film defects on mask blanks is a key for the commercial success of EUVL. It is known that particles are added to the Mo—Si multilayer film during the fabrication process. There is a large effort to reduce this contamination, but results are not sufficient, and defects continue to be a major mask yield limiter. All suggested repair strategies need to know the out-of-plane position of the defects in the multilayer.

65 Claims, 6 Drawing Sheets

METHOD FOR CHARACTERIZING MASK DEFECTS USING IMAGE RECONSTRUCTION FROM X-RAY DIFFRACTION PATTERNS

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to defect repair, particularly in EUVL multilayers, and more specifically, it relates to methods for determining the location of such defects.

2. Description of Related Art

Extreme ultraviolet (EUV) lithography is the top contender for next generation lithography in high-volume semiconductor manufacturing for the 35 nm node and beyond. It utilizes 13.4 nm radiation as the exposure light source and employs Mo—Si multilayer stacks as the reflector for both optic mirrors and mask blanks.

Referring to FIG. 1A, EUV mask blanks are fabricated by depositing a reflective Mo/Si multilayer film 10 onto a super-polished substrate 12. Localized defects in this thin film can significantly alter the reflected field and introduce errors in the printed image. When input beam 14 is reflected, as depicted by reflected beam 18, from the multilayer film 10 of FIG. 1A, a defect 16 located near the top of the multilayer prevents a portion of the beam from being reflected, resulting in a reduction in amplitude of reflected beam 18. When input beam 20 is reflected, as depicted by reflected beam 22, from the multilayer film 20 (on substrate 26) of FIG. 1A, a defect 28 located near the lower portion of the multilayer prevents a portion of beam from being reflected, resulting in a phase defect in reflected beam 22. Several techniques for repairing localized defects have been suggested (see U.S. patent application Ser. No. 09/669,390, titled: "Repair of phase defects in EUVL mask blanks using spatially-resolved, enhanced interdiffusion in the multilayer coatings," incorporated herein by reference and U.S. patent application Ser. No. 09/896,722, titled: "Method to repair localized amplitude defects in EUVL mask blanks," incorporated herein by reference. The applicability of these techniques depends on the position of the defects in the multilayer stack. Phase defects 30 and 32, as shown in FIGS. 2A and 2B respectively, are repaired by contracting the volume above the defect through local heating, as shown in FIG. 2B. On the other hand, an amplitude defect 40, as shown in FIG. 3A, is repaired by removing the defect along with the surrounding multilayer altogether to leave a removed area 42, as shown in FIG. 3B, and the top surface of the removed area is capped with a protective layer 44 to prevent oxidation, as shown in FIG. 3C. The right repair technique is selected, depending on the out-of-plane position of the defect in the multilayer, to prevent the repair zone from becoming worse or even un-repairable.

Several techniques and tools have been developed to determine the in-plane position of defects. However, little work has been done to determine the out-of-plane defect position in a non-destructive way. Other techniques, such as cross-sectional transmission electron microscopy (TEM) using a focused ion beam (FIB) are destructive and render the mask useless. An aerial image microscope (AIMS tool) can image the defect, but cannot uniquely determine the position of the defect in the multilayer stack.

It is desirable to provide a cost-efficient, non-destructive way to locate, characterize and repair defects in thin films.

SUMMARY OF THE INVENTION

It is an object of the invention to provide a method for computationally locating a defect in a sample so that an appropriate repair technique can be selected and applied to repair the defect.

It is another object to provide a cost-efficient, non-destructive way to locate and characterize defects in thin films.

These and other objects will be apparent to those skilled in the art based on the disclosure herein.

An embodiment of the invention is a method for characterizing and repairing defects using image reconstruction from diffraction patterns. A sample is provided for testing for the location of a defect. The sample is illuminated on a series of areas with a beam of typically X-ray light or electrons to create a series of two-dimensional diffraction patterns. A three-dimensional diffraction pattern is produced from the two-dimensional diffraction patterns. Conventional diffraction imaging algorithms are used to compute a reconstructed image of the sample from the three-dimensional diffraction pattern. This reconstructed image allows a determination of the location of a defect within the sample. Once the location of the defect has been determined, an appropriate repair technique can be selected and applied from a number of known repair techniques. The present invention is not limited to Mo/Si multilayers but can also be used to characterize defects in other thin films (e.g., magnetic thins film, Cu films for semiconductor BEoL (back-end of line) applications etc.).

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The present invention applies techniques for image reconstruction from X-ray diffraction patterns to produce three-dimensional images of defects in EUVL multilayer films. Techniques for image reconstruction from X-ray diffraction patterns are described in "Image reconstruction from electron and X-ray diffraction patterns using iterative algorithms: experiment and simulation," Ultramicroscopy, Vol. 90, Issues 2–3, February 2002, Pages 171–195, incorporated herein by reference and in "Phase retrieval algorithms: a comparison," Applied Optics, Vol. 21, No. 15, Aug. 1, 1982, Pages 2758–2769, incorporated herein by reference. The reconstructed image will give information about the defect position and the diffraction strength of the defect The positional information can be used to select the correct defect repair technique.

Figure 1A:
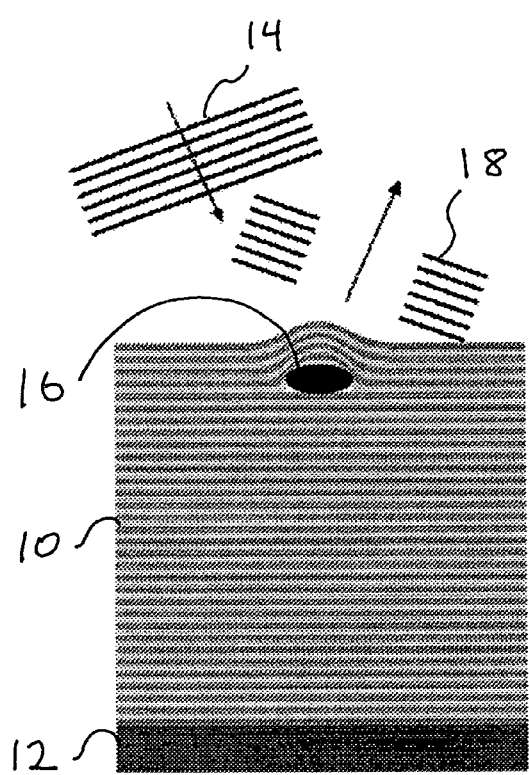
FIG. 1A shows a prior art amplitude defect.
Figure 1B:
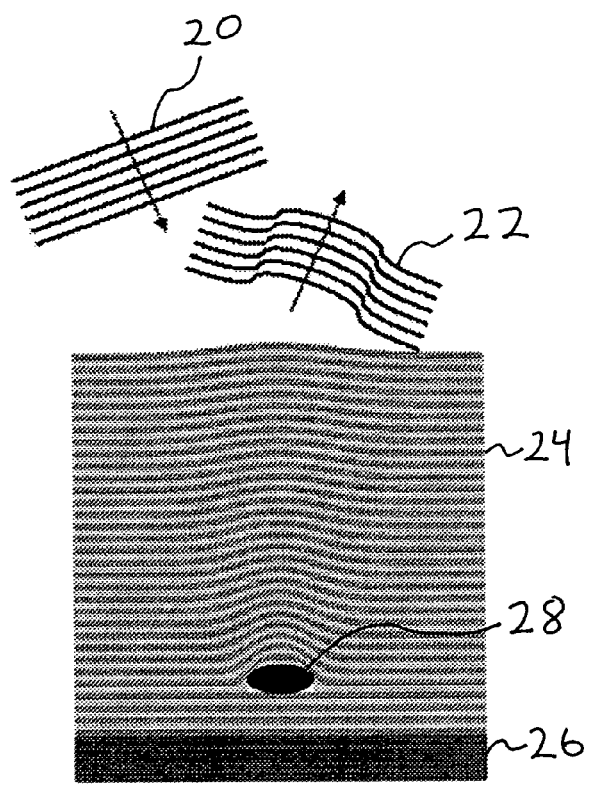
FIG. 1B shows a prior art phase defect.
Figure 2A:
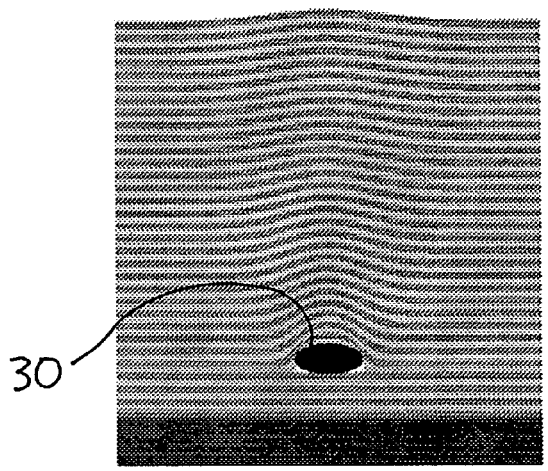
FIG. 2A shows a prior art phase defect.
Figure 2B:
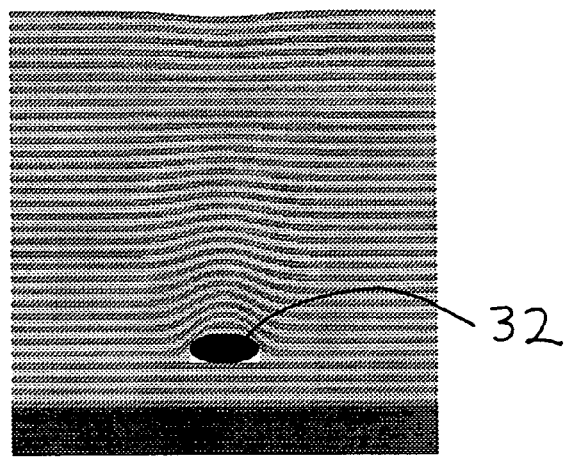
FIG. 2B shows a prior art technique for repairing a phase defect.
Figure 3A:
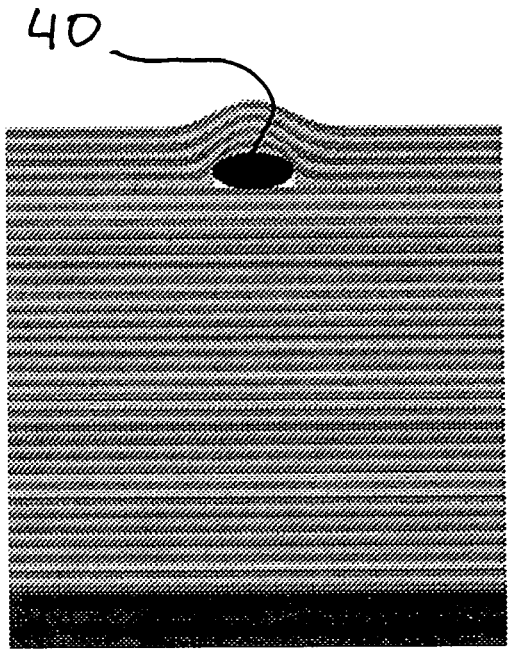
FIG. 3A shows a prior art amplitude defect.
Figure 3B:
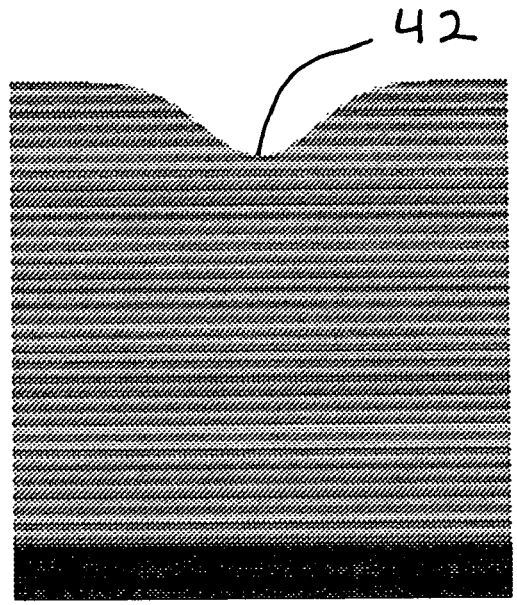
FIG. 3B shows a prior art technique for removing an amplitude defect.
Figure 3C:
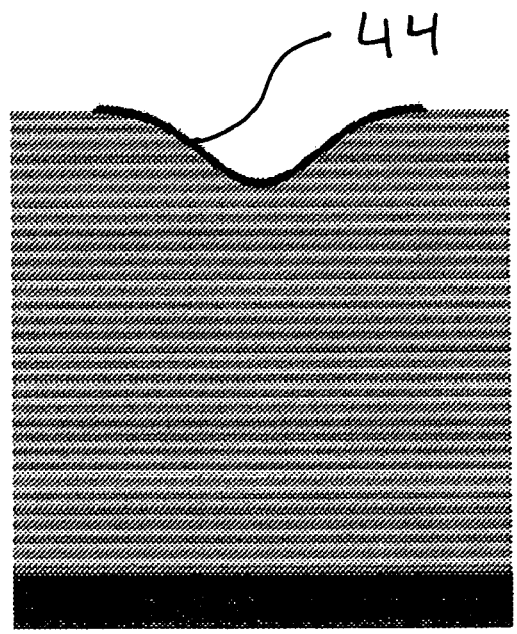
FIG. 3C shows a prior art repaired amplitude defect (protected by a cap layer).
Figure 4A:
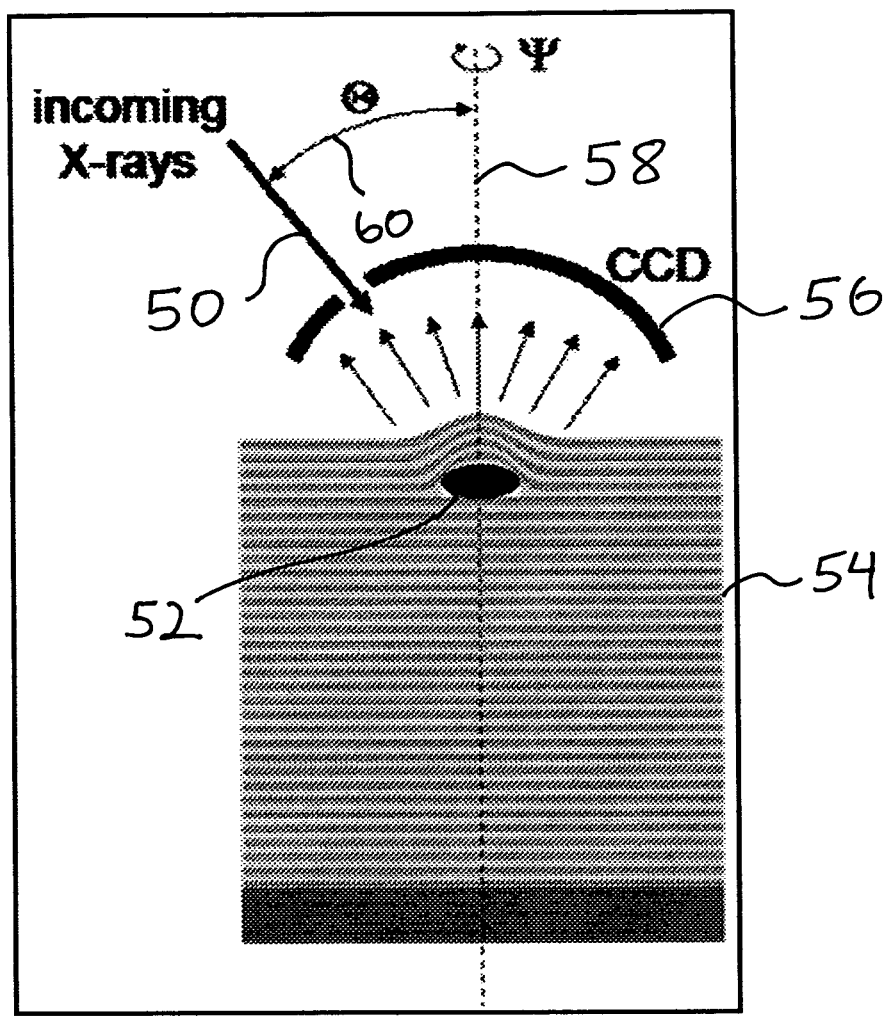
FIG. 4A shows an example experimental setup for the present invention.
Figure 4B:
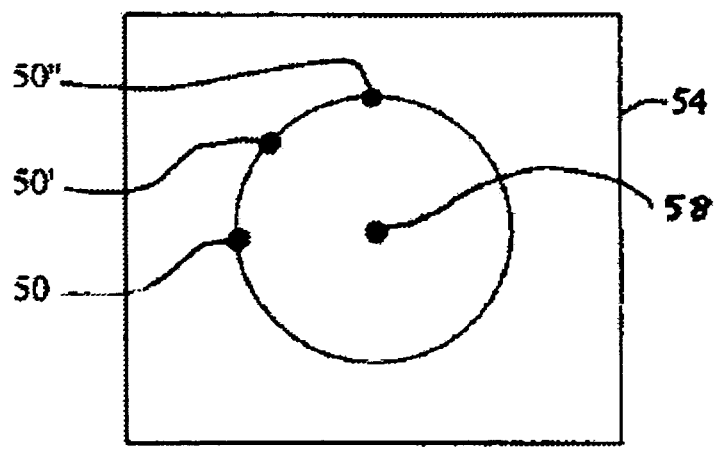
FIG. 4B shows the illumination of a series of areas of the sample of FIG. 4A.
Figure 5A:
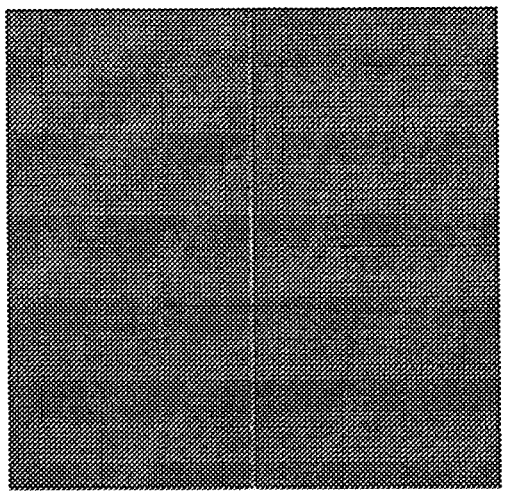
FIG. 5A shows an example diffraction pattern from a defect-free multilayer.
Figure 5B:
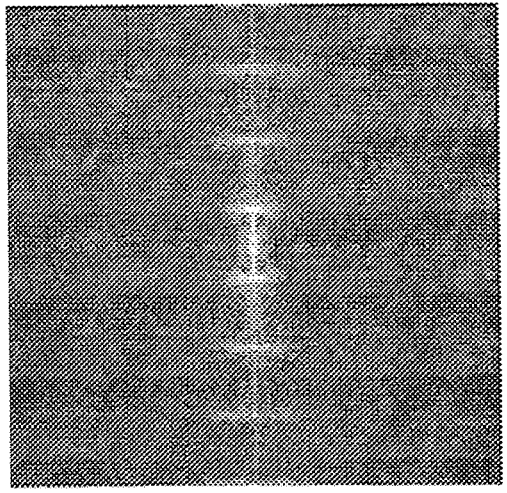
FIG. 5B–5D shows a series of diffraction pattern from a multilayer with a defect.
Figure 5C:
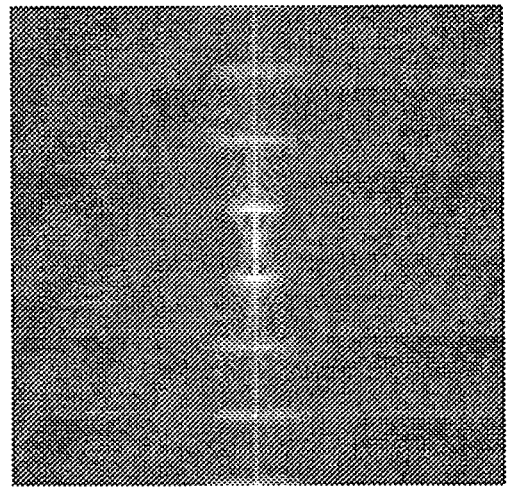
Figure 5D:
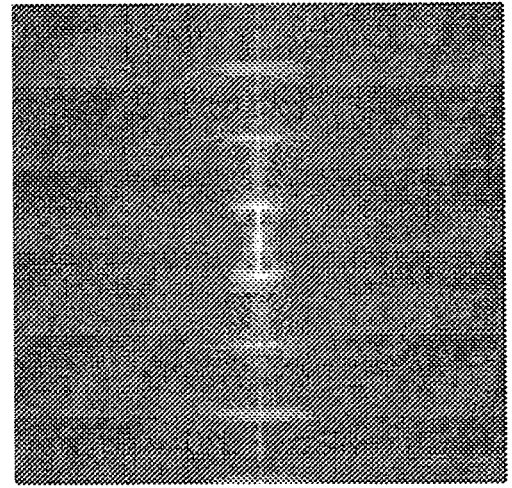
Figure 7:
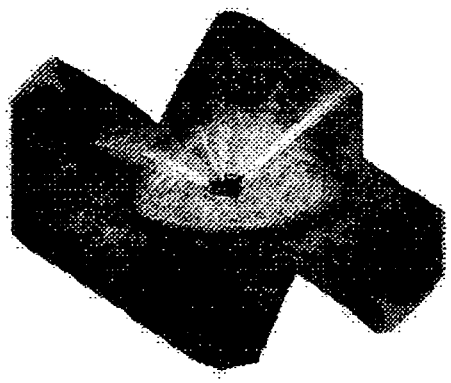
FIG. 7 shows an exemplary three-dimensional diffraction pattern.

An experimental setup is shown in FIG. 4A. An incoming X-ray beam 50 illuminates an area around a defect 52. It is preferable to use a focused beam. The beam is elastically scattered by the multilayer 54 and the defect 52, and creates a two-dimensional diffraction pattern, which is captured on a CCD 56. FIG. 4B is a top view of the multilayer 54 of FIG. 4A and shows the illumination of a series of areas of the sample of FIG. 4A by rotating the incoming x-rays (50,50' and 50") or multilayer 54 around axis 58. FIG. 5A shows a two-dimensional diffraction pattern of a defect-free multilayer, and FIGS. 5B–5D show a series of diffraction patterns from a multilayer with a defect. Referring again to FIG. 4A, to obtain a three-dimensional diffraction pattern then, the sample or the beam is rotated around $\Psi$, which is depicted as an axis 58, where $\Theta$ is depicted as the angular position 60 of incoming x-rays 50, with respect to axis 58, and at a series of positions a two-dimensional diffraction pattern is recorded. These diffraction patterns are parts of the Ewald sphere in reciprocal space, and rotating the sample will lead to exploring the full reciprocal space by rotating the Ewald sphere. FIG. 7 shows an exemplary three-dimensional diffraction pattern.

Figure 6A:
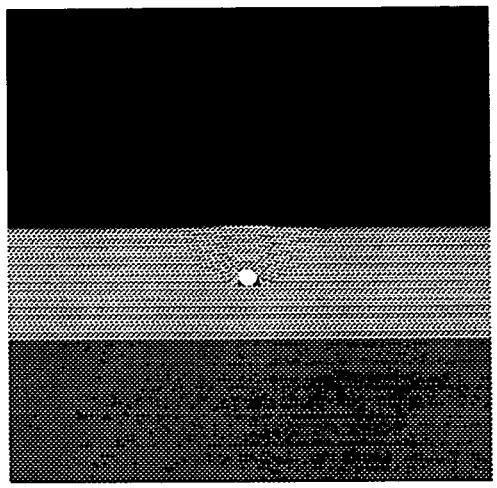
FIG. 6A shows an example defect in a multilayer.
Figure 6B:
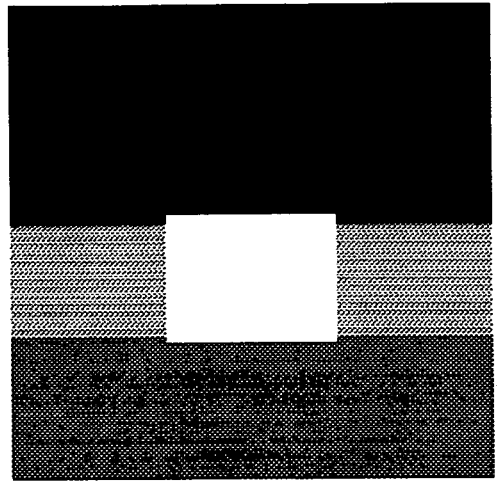
FIG. 6B shows a support function for reconstruction.
Figure 6C:
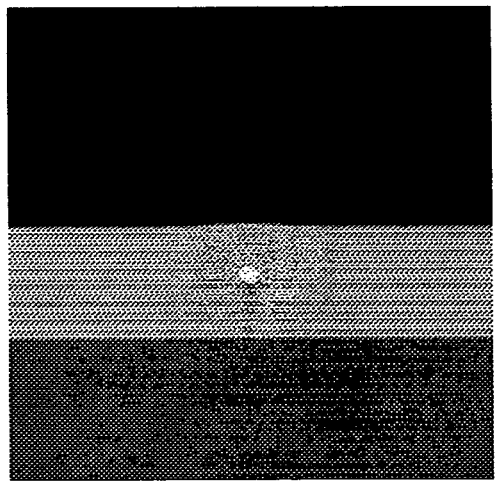
FIG. 6C shows a reconstructed image.

Standard image reconstruction techniques, e.g., as described in the incorporated papers, are then used to reconstruct the three-dimensional real-space image from the three-dimensional diffraction pattern. Since the CCD only records the amplitudes of the light and not the phases, this problem is similar to the fundamental phase problem of crystallography. As an example, a defect and the surrounding multilayer was constructed for a fictitious two-dimensional case. FIG. 6A shows a cross-section of the image to be reconstructed. The diffraction pattern was calculated from this image, and the amplitudes were used to reconstruct the image. For the reconstruction the information was used that the volume away from the defect is an unperturbed multilayer. This fact is similar to the so-called support function. The support function is shown in FIG. 6B. The center is unknown, but the frame around it is unperturbed multilayer, the substrate, and vacuum. Unlike the standard algorithms, the support function is not zero outside of the center. An iteration is made between diffraction and real space to solve the problem using FFT, and at each step the known information (support function and amplitudes of the diffraction pattern) is introduced. This iterative algorithm eventually converges, as shown in FIG. 6C. This clearly locates the defect in the multilayer film. Further information is also obtained about the diffraction strength of the defect.

Since light is readily absorbed by Mo/Si, it is desirable in such a case to use light that is in resonance with the multilayer. One could use EUV light (13.7 nm), of course, but it is advantageous at times to use a harmonics of that to increase the number of photons that escape the film.

In the following we will first describe a method to repair phase defects, and then describe a method to repair amplitude defects.

The present invention is a method to repair defects in the multilayer-coated reticles used in extreme ultraviolet lithography systems. The method consists of depositing energy in the multilayer coating in the vicinity of the defect with high lateral spatial resolution. This can be accomplished using a focused electron beam, focused ion beam, focused electromagnetic radiation or through direct contact with an electrode. If the multilayer film consists of Mo/Si or another appropriate material combination, the absorbed energy will cause a structural modification, producing a localized change in the film thickness. An appropriate material combination would be defined by materials that undergo structural modification at elevated temperatures that results in a local change in density. This could be due to the formation of a compound, as in the case of Mo/Si, or could be simply a phase transformation. Note that either an increase or decrease in the density is useable. Mo/Si has an increase in density, thereby producing a film contraction. If the density decreases upon heating then the invention would be used to expand the film in the region of valleys and smooth the edges in the region of hills. The change in film thickness can be controlled with sub-nanometer accuracy by adjusting the energy dose. The lateral spatial resolution of the thickness modification is controlled by the localization of the energy deposition. The film thickness is adjusted locally to correct the perturbation of the reflected field. For example, in the case where the structural modification is a local contraction of the film, the repair of a defect consists of flattening a mound or spreading out the sides of a depression. The defect repair can be applied directly to the reflective multilayer coating or to a buffer layer consisting of a multilayer film deposited below the reflective multilayer. This invention can be used to repair multilayer defects in reticle blanks or in fully patterned reticles, since the highest temperature used in the repair process can be maintained well below the melting temperature of the metal absorber layer.

In order to assess the viability of the present invention, finite element simulations were performed for the case of an electron beam impinging on a localized area of a Mo/Si multilayer film. In this case the structural modification is a local contraction of the multilayer period due to silicide formation, which produces an indentation in the film in the vicinity of the electron beam. In a finite element simulation of the deformation of a Mo/Si multilayer film produced by a 10 msec exposure to an electron beam of radius 25 nm, energy 10 kV, and current 3 µA, a depression at the surface was 12 nm, yet the contraction of each multilayer period is only 0.5 nm. This modification of the multilayer structure can be used to correct the phase of the reflected field without significantly altering the reflected amplitude. The size of the depression at the surface can be controlled by controlling the exposure time. More information on these simulations is described below.

More specifically, finite element analysis was used to simulate the temperature increase in a Mo/Si multilayer film due to the injection of current by an electron beam. The calculations were performed using the commercial FlexPDE software sold by PDE Solutions, Inc. See www.pdesolutions.com. The Mo/Si multilayer film was modeled in cylindrical coordinates (2D) as a disk of thickness 280 nm and radius 10 µm on a Si substrate of thickness 1.12 µm. The multilayer film, which actually is composed of 40 Mo/Si periods each having a thickness of 7.0 nm, was treated as a single isotropic film for the purpose of the FEM modeling. The material properties of the Mo/Si film and the Si substrate are listed in Table I.

TABLE I below shows values for the thermal conductivity K, the mass density p, the specific heat cp and the conductivity σ used in the FEM modeling.

| Material | κ(W/cm-° K) | ρ(gm/cm$^3$) | c$_P$(J/gm-° K) | σ(1/Ω-cm) |
|---|---|---|---|---|
| Mo/Si ML Film | 1.45 | 5.48 | 0.53 | $1 \times 10^4$ |
| Si substrate | 1.49 | 2.33 | 0.71 | 1 |

The time-dependent temperature profile T(r,z;t) within the multilayer film was determined by solving the thermal diffusion equation:

$$\frac{1}{r}\frac{\partial}{\partial r}\left(\kappa\frac{\partial T}{\partial r}\right) + \frac{\partial}{\partial z}\left(\kappa\frac{\partial T}{\partial z}\right) - \rho c_P \frac{\partial T}{\partial t} + H(r,z;t) = 0 \quad (1)$$

Here H is the heat source. The electron beam voltage was chosen to be sufficiently high (10 kV) so that the electron range would approximately match the thickness of the multilayer film. Then it was assumed that the energy was deposited uniformly through the film, within a cylinder of radius r0=25 nm. (This oversimplified picture neglects the scattering of the electrons within the film, which could be significant). In this model the heat deposited by the electron beam per unit volume was given by, $$H = \frac{IV}{\pi r_0^2 \tau} \quad (2)$$

Here I and V are the respective current and voltage of the electron beam and τ is the thickness of the multilayer film.

The time required for heat to diffuse a distance x is given by $x^2 \rho c_p/\kappa$. Inserting the values from Table I, it is seen that heat diffuses a micron in 20 ns. Hence, over the physical dimensions of this problem, the transient temperature dependence only lasts for tens of nanoseconds. Since such short timescales are not of interest, Eq. (1) was simplified by dropping the dT/dt term and just solved for the steady state temperature profile. The boundary conditions used in the calculations were that the bottom and sides of the substrate and the sides of the multilayer film were maintained at a constant ambient temperature of 300° K. These surfaces were also defined to be electrical ground (V=0). The top surface of the multilayer film was assumed to be thermally insulated (i.e., radiative cooling was neglected).

The current density was adjusted to produce peak temperatures sufficiently high (>800° K.) to activate the silicide formation that causes the contraction of the multilayer film.

Once the temperature profile is known, it is straightforward to calculate the contraction of the multilayer film due to silicide formation. The reaction of Mo and Si at the interfaces is rate limited by thermally activated interdiffusion (See "Silicide Layer Growth Rates in Mo/Si Multilayers", R. S. Rosen, D. G. Stearns, M. A. Viliardos, M. E. Kassner, S. P. Vernon and Y. Cheng, Appl. Optics 32, 6975 (1993), incorporated herein by reference.) The width of the interlayer increases with time according to:

$$w^2 = w_0^2 + 2Dt \quad (3)$$

Here $w_0$=1.0 nm is the starting thickness of the interlayers in as-deposited films. The interdiffusion coefficient D is given by, $$D = D_0 \exp(-E_A/kT) \quad (4)$$

Where $D_0$=50 cm$^2$/s and $E_A$=2.4 eV for Mo/Si multilayer films. The formation of the silicide interlayer involves densification that leads to a contraction of the multilayer period. The local change in the period is given by, $$\Delta\Lambda = \Lambda_0 - \alpha(w - w_0) \quad (5)$$

Here α is the contraction factor that depends on the particular silicide compound that is formed. In this study, α=0.38 is used, which corresponds to the contraction that occurs upon the formation of MoSi$_2$.

The growth of the silicide interlayer has an approximately square root dependence on the time that the film is subjected to heating, which will be referred to as the exposure time. Note that because the thermal response is so rapid, the transient heating and cooling times can be neglected. The interlayer has a maximum thickness at the surface of the film in the center of the current injection (r=0), and is approximately twice as thick as the as-deposited interlayer. The electron beam creates significant interlayer growth nearly half way through the entire thickness of the film. This is of course due to the penetration of the electron beam, and the fairly uniform heating through the thickness of the film. Because the interlayer growth is in an activated process, it is only significant in those regions reaching temperatures greater than ~800° K.

The local contraction of the multilayer period produces an indentation in the film in the vicinity of the electron beam. With a structural deformation in a Mo/Si multilayer film resulting from a 10 ms exposure (I=3 μA, V=10 kV), the depression at the surface is 12 nm deep, and the contraction of each multilayer period, ΔΛ, is less than 0.5 nm. Consequently the primary effect of such a deformation on the EUV reflectivity of the multilayer film will be to cause a local phase perturbation. For larger deformations there will also be a decrease in the reflectivity due to the decrease in contrast at the multilayer interfaces. Note also that the lateral width of the deformation is contained within the region of the electron beam. The depth of the deformation is most easily controlled by adjusting the exposure time. By adjusting the exposure time and the footprint, the detailed shape of the deformation and the corresponding phase shift can be accurately controlled.

An electron beam of moderate voltage (~10 kV) can be used to contract the period of a Mo/Si reflective coating within a small spot defined basically by the footprint of the beam. (For Mo/Si, the key physical requirement on the energy deposition is the spatial resolution, i.e., small spot size, and energy sufficient to raise the temperature by hundreds of degrees. In the case of Mo/Si this works out to a deposited power in the range of 1–100 mW.) The contraction of the period, due to thermally activated silicide formation at the multilayer interfaces, occurs through approximately half the thickness of the film (20 periods). This produces a controllable indentation at the top surface having a depth that can exceed 10 nm. Since the film contraction generated by the electron beam is distributed over many periods, the primary effect of the deformation on the EUV reflectivity is a local phase shift of the reflected field. Bumps due to coating over particles can be repaired by directly writing on top of them to shrink the film back to its correct position. Indentations due to coating over pits and scratches could be repaired by contracting the film at the edges and thereby smooth out the defect to mitigate the phase contrast. In fact, it might indeed be possible to use this technique to repair the Mo/Si multilayer film underneath an existing metal absorber layer, since the metal layer should not be affected by exposure to these temperatures.

The requirements of microamps of current at 10 kV are difficult to achieve within a spot size of ~50 nm. One solution is to use field emission from a carbon nanotube. These nanotubes are typically tens of nanometers in diameter and are stable, high current field emitters capable of delivering microamps of current (See A. G. Rinzler, J. H. Hafner, P. Nikolaev, L. Lou, S. G. Kim, D Tomanek, P. Nordlander, D. T. Colbert and R. E. Smalley, "Unraveling Nanotubes: Field Emission from an Atomic Wire", Science 269, 1550 (1995) incorporated herein by reference. The nanotube could be integrated into the head of a scanning probe microscope, and proximity focusing could be used to steer the extracted current into a small spot on the surface of the film. The scanning probe microscope would be used to locate and monitor the repair of the mask defect Examples of carbon nanotubes are described in copending U.S. patent application Ser. No. 09/669,948, titled "A High-Current, High-Voltage, Small Diameter Electron Beam Source Obtained By Field Emission From, And Used In Close Proximity To, A Single Carbon Nanotube," incorporated herein by reference.

Now we will describe a method to repair amplitude defects.

An amplitude defect in a reflective multilayer coating can be caused by the imbedding of a particle near or at the top of the coating. The particle reduces the local reflectivity of the coating in two ways:

1. The particle directly shadows the underlying layers, and thereby reduces the reflected field due to the absorption of light by the particle.

2. The particle damages the multilayer structure in its vicinity, either in the actual imbedding process, or during the growth of the multilayer around the particle. There is no contribution to the reflected field from the damaged region of the multilayer, and hence the local reflectivity is reduced due to absorption in the damaged region.

Even in the case where the particle does not remain imbedded in the coating, the residual damaged region of the multilayer acts as an amplitude defect In this case, the defect will physically appear as a pit or scratch in the top of the multilayer coating. It is also important to emphasize that the repair of amplitude defects in the multilayer coating is to be performed on the mask blank, prior to the deposition of the absorber layer.

The basic principle of the repair method is to restore the local reflectivity by removing the particle (if it exists) and the damaged part of the coating, while exposing the intact underlying layers of the multilayer coating. This process must satisfy two constraints. First, the intact underlying layers must not be damaged in the repair process. Second, the repaired region must not produce a significant variation of contrast in the bright field intensity of the lithographic image.

The repair method can be generally divided into two steps. In the first step, the imbedded particle is physically removed by milling using a focused ion beam (FIB). See "Micro-machining using a focused ion beam" R. J. Young, Vacuum 44, 353 (1993), incorporated herein by reference. This step is not necessary if the defect is a pit or scratch. The FIB has a gas source (consisting of, for example, He, Ne, Ar, Xe, F, Cl, I, Br), or a liquid metal source (consisting of, for example, Ga). Using a FIB operated near normal incidence, material can be removed with a depth resolution of 10 nm and a lateral resolution of 100 nm. Typical operating parameters for a Ga ion source are a beam voltage of 25 keV, a beam current of 40 pA, a beam diameter of 50 nm, and a milling rate of 10 $\mu m^3$/nA-min. An advantage of this approach is that the FIB can simultaneously provide high-resolution images of the defect, which is useful for alignment and monitoring of the repair process. A potential problem of using the FIB is that Ga atoms are implanted into the coating to a depth of approximately 10 nm beneath the surface. This reduces the optical contrast of the Mo and Si layers directly underneath the amplitude defect, and requires that these layers be subsequently removed. A possible way to mitigate the implantation problem is to use a lower beam voltage at the cost of a larger beam diameter.

At this stage there is a small hole in the multilayer coating, having a depth sufficient to remove the imbedded particle. The remaining structure is still defective because the FIB milling process produces collateral damage in the vicinity of the hole due to implantation and redeposition. Furthermore, the hole itself will produce a phase perturbation in the reflected field. To complete the repair of the defect it is necessary to remove the remaining damaged part of the multilayer coating in the vicinity of the hole, and to smooth out the contour of the surface of the coating. Specifically, the second step of the repair process replaces the hole and the surrounding damaged part of the coating with a large-diameter (10 $\mu$m-1 mm-diameter), shallow (typically <150 nm-depth) crater.

The crater is etched in the multilayer coating using a low-voltage (<5000 V) ion beam at a low angle of incidence (<20 degrees from the coating surface). This beam configuration is commonly used for the preparation of thin cross-sectional samples for transmission electron microscopy. See "Precision Ion Polishing System—A New Instrument For TEM Specimen Preparation Of Materials" R. Alani and P. R. Swann, Mat Res. Symp. Proc. 254,43 (1992), incorporated herein by reference. It is well known that this technique can produce a shallow crater of controlled depth having a very smooth and gradual surface slope. The ion beam can be the same as that used for removing the particle (for example, a Ga-source FIB) or a second ion beam having a gas source (consisting of, e.g., He, Ne, Ar, Xe, F, Cl, I, Br). The beam can be relatively large (up to 1 mm diameter) and can be rotated with respect to the mask to improve the uniformity of the etching process.

The conditions of low voltage and low angle of incidence for the ion beam are critical for avoiding damage to the underlying layers in the multilayer coating. One important requirement is that the temperature of the coating remains below approximately 200° C. throughout the repair process, since higher temperatures can activate structural relaxation at the Mo—Si interfaces. See "Stress, Reflectance, And Temporal Stability Of Sputter Deposited Mo/Si And Mo/Be Multilayer Films For Extreme Ultraviolet Lithography", P. B. Mirkarimi, Opt Eng. 38, 1246 (1999). It has been shown that etching Si using a Ar ion beam of 4 kV and 1 mA at an grazing angle of 20 degrees increases the temperature of the sample to ~85° C. See D. Bahnck and R. Hull, Mat Res. Soc. Symp. Proc. 199, 253 (1990) (Title: "Experimental measurement of transmission electron microscope specimen temperature during ion milling"). The temperature increase is expected to be similar for a Mo—Si multilayer coating, and even smaller for lower beam voltage and lower incidence angles.

The other important advantage of using low voltage and low angle of incidence in the etching process is that it minimizes the damage to the layers exposed at the surface of the crater. There is always some mixing induced by the ion beam at the surface. However, studies of Ar ion etching of Si have shown that the thickness of this damaged surface region is in the range of 1–2 nm for a beam voltage of 2 kV and a grazing angle of 14 degrees. See T. Schuhrke et al., Ultramicroscopy 41,429 (1992) (Title: "Investigation of surface amorphization of silicon wafers during ion-milling"). In the case of the Mo—Si multilayer coating, the mixing induced by the ion beam is likely to result in a thin surface layer of $MoSi_2$. This will actually provide a benefit of protecting the pure Mo and Si layers from oxidation. Alternatively, after the ion milling step a thin (1–2 nm) layer of Si can be deposited on top of the exposed multilayer coating in the repaired region, to limit the oxidation at the surface.

In order to evaluate the efficacy of the repair, the effect of the residual crater on the lithographic image must be considered. The field reflected in the region of the crater will have a small modulation in phase and amplitude that will produce a small contrast in the bright field intensity at the wafer. The phase modulation is due to the slope of the surface inside the crater. The amplitude modulation arises from three effects. First, the reflectivity changes with the composition of the top layer and hence is modulated along rings within the surface of the crater, corresponding to the regions where the Mo and Si layers are alternately exposed. Second, the reflectivity in the crater is reduced due to the absorption of the surface layer, which is assumed to be $MoSi_2$, produced by ion beam mixing. Third, the reflectivity decreases with the number of bilayers that are remaining in the multilayer coating, which is a minimum in the bottom of the crater. Since the size of the crater (>10 μm radius) is much larger than the resolution element, δ, at the mask (δ~200 nm), the residual effect of the repair on the imaging performance will be to cause a local variation in the critical dimension (CD). Using a simple threshold model for the resist, the CD is determined by the width of the aerial image at the threshold intensity. It is evident that the change in the bright field contrast associated with the repaired region produces an increase in the CD. An estimate of the increase in CD produced by a bright field contrast variation ΔC is, $$\Delta CD(\%) = 0.5 \Delta C(\%) \tag{6}$$

The total budget for the allowable CD variation in EUVL is expected to be 5%. This must be divided among many sources such as flare, pattern error, optical distortion and resist non-uniformity. Hence the CD error budget available to mask defects is more likely to be in the range of ~2%. Using Eq. (1), this implies that the contrast variation in the bright field intensity produced by the repaired region of the multilayer coating should be less than ~4%.

The different contributions to the bright field contrast variation must be considered. The undamaged multilayer coating has a top layer of Si (actually $SiO_2$ after oxidation when exposed to atmosphere). The top layer in the repaired region will alternate between Mo and Si with increasing depth of the crater. The contrast variation is different for the Mo and Si top layers, but generally increases with increasing $MoSi_2$ thickness. A similar behavior will occur if there is an oxidized protective layer of Si deposited on the surface of the repaired region.

Another source of contrast variation within the repaired region is the decreased number of layer pairs in the multilayer coating. It has been shown that where the undamaged coating has 60 layer pairs, the removal of 20 bilayers results in a contrast variation of less than 1%.

Finally, the shallow crater in the surface of the repaired coating perturbs the phase of the reflected field, resulting in an additional variation of the contrast in the lithographic image. Let us assume that the depth profile of the crater produced by the repair process is Gaussian with a maximum depth of N bilayers and a radius w. Then the resulting phase perturbation, φ(r), in the reflected field is given by, $$\phi(r) = 4\pi N \frac{(n-1)}{n} \exp(-r^2/w^2) \tag{7}$$

where λ is the vacuum wavelength of the EUV light and n is the average index of refraction of the multilayer coating (n=0.97 for Mo/Si). The image intensity at a defocus value of Δz is related to the second derivative of the phase according to [J. M. Cowley, "Diffraction Physics, $2^{nd}$ ed." (North-Holland, Amsterdam, 1984) p. 61], $$I(r) = 1 + \Delta z \frac{\lambda}{2\pi} \nabla^2 \phi(r) = 1 + \frac{\lambda^2}{2\pi (NA)^2} \nabla^2 \phi(r) = 1 + \frac{\delta^2}{2\pi} \nabla^2 \phi(r) \tag{8}$$

Here we have used for the defocus position a value of $\Delta z = \lambda/(NA)^2$ which is twice the conventional depth of focus (this is a very conservative case), and we have defined the resolution element at the mask to be δ=λ/(NA). Substituting into Eq. (2) from Eq. (1) we obtain, $$I(r) = 1 - 4N\delta^2 \frac{(n-1)}{n} \frac{w^2 - 2r^2}{w^4} \exp(-r^2/w^2) \tag{9}$$

The contrast variation in the image intensity is determined to be, $$\Delta C \equiv \frac{I_{MAX} - I_{MIN}}{I_{MAX} + I_{MIN}} = 5.78 \, N \frac{(n-1)}{n} \frac{\delta^2}{w^2}. \tag{10}$$

Now we can estimate the image contrast due to the phase error produced by the profile of the repaired region for realistic lithographic parameters. Consider an operating wavelength of 13 nm and a numerical aperture on the image side of 0.25, which corresponds to a resolution element on the mask of approximately 200 nm. The variation of the contrast with the maximum depth of the crater is shown in FIG. 6A for several different values of the radius w. It is evident that the contrast increases rapidly with increasing depth. However, when the radius is 5 μm the contrast remains less than 1% for a depth as large as 30 bilayers. A crater having a radius greater than 5 μm, or a diameter greater than 10 μm, will produce a contrast variation in the image intensity of less than 1%.

Since the total allowable bright field contrast variation produced by the repaired defect is 4%, then the contributions from each of the sources described above must be limited to around 1%. This sets fairly narrow specifications for the structure of the repaired multilayer. The consideration of the modulation of the reflectivity due to the top layer requires that the thickness of the MoSi2 surface layer be ~2 nm or less. A protective Si layer deposited on the surface to limit oxidation can be approximately twice as thick, or up to 4 nm. The dependence of the contrast on the number of bilayers removed in the repair process restricts the crater to having a maximum depth of ~20 bilayers. A crater that is 20 bilayers deep must have a diameter greater than 10 µm to keep the phase contrast below the 1% value. It is thus concluded that the repair method of removing an amplitude defect and replacing it with a shallow crater is viable in terms of its effect on the lithographic image. However, the resulting shallow crater is required to have a maximum depth of 20 bilayers and a minimum diameter of approximately 10 µm. This will maintain the local variation in the CD to be less than 2%, well within the EUVL error budget Note that there is no upper limit to the allowable diameter of the crater, and that in practice it could be more convenient to have the diameter of the crater be considerably larger than 10 µm, even as large as 1 mm. This would allow the use of a larger-diameter ion beam for the etching of the crater, i.e., the ion beam diameter could be as large as the crater diameter of 1 mm.

The foregoing description of the invention has been presented for purposes of illustration and description and is not intended to be exhaustive or to the invention to the precise form disclosed. Many modifications and ions are possible in light of the above teaching. The embodiments disclosed meant only to explain the principles of the invention and its practical cation to thereby enable others skilled in the art to best use the invention in us embodiments and with various modifications suited to the particular use contemplated. The scope of the invention is to be defined by the following claims.

I claim:

1. A method for characterizing and repairing defects using image reconstruction from diffraction patterns, comprising:
    providing a sample for testing for the location of a defect within said sample;
    illuminating, with a beam, a series of areas of said sample, to create a series of two-dimensional diffraction patterns;
    producing a three-dimensional diffraction pattern from said series of two-dimensional diffraction patterns;
    computationally producing a reconstructed image of said sample from said three-dimensional diffraction pattern;
    determining the location of said defect within said sample from said reconstructed image;
    repairing said defect by applying an appropriate repair technique depending upon the location of said defect within said sample, wherein said sample or said beam is rotated around an axis, wherein Θ is the angular position of said beam with respect to said axis, and
    recording a two-dimensional diffraction pattern at said series of positions.

2. The method of claim 1, wherein said beam comprises an X-ray beam.

3. The method of claim 1, wherein said beam comprises extreme ultraviolet light.

4. The method of claim 3, wherein said extreme ultraviolet light comprises a wavelength of 13.7 nm.

5. The method of claim 3, wherein said beam comprises a harmonic of said extreme ultraviolet light.

6. The method of claim 5, wherein said beam comprises a harmonic of 13.7 nm.

7. The method of claim 1, wherein said beam comprises an electron beam.

8. The method of claim 1, wherein said beam is elastically scattered by said sample.

9. The method of claim 1, further comprising capturing said series of two-dimensional diffraction patterns prior to producing a three-dimensional diffraction pattern.

10. The method of claim 9, wherein the step of capturing said series of two-dimensional diffraction patterns is carried out with a CCD camera.

11. The method of claim 1, wherein said sample comprises an EUVL multilayer film.

12. The method of claim 1, wherein said beam is focused.

13. The method of claim 1, wherein the step of computationally producing a reconstructed image includes applying a technique for image reconstruction from diffraction patterns on said three-dimensional diffraction pattern.

14. The method of claim 13, wherein said technique for image reconstruction from diffraction patterns comprises an iterative algorithm.

15. The method of claim 13, wherein said technique for image reconstruction from diffraction patterns comprises a phase retrieval algorithm.

16. The method of claim 1, wherein said sample comprises a multilayer of Mo/Si.

17. The method of claim 1, wherein said sample a magnetic thin film.

18. The method of claim 1, wherein said sample comprises a Cu film.

19. The method of claim 1, wherein said sample comprises a reticle with a thin film coating having a thickness, wherein said reticle is for use in an extreme ultraviolet lithography (EUVL) system, wherein the step of repairing said defect comprises changing the thickness of said thin film coating in the vicinity of said defect.

20. The method of claim 19, wherein said thin film coating comprises a multilayer coating having multiple layer boundaries, wherein the step of changing the thickness of said thin film coating in the vicinity of said defect includes interdiffusing at least one layer boundary of said layer boundaries.

21. The method of claim 19, wherein said thin film coating comprises a multilayer coating having multiple layer boundaries, wherein the step of changing the thickness of said coating in the vicinity of said defect includes altering the density of at least one layer of said multilayer coating.

22. The method of claim 19, wherein said thin film coating comprises a multilayer coating having multiple layer boundaries, wherein the step of changing the thickness of said thin film coating in the vicinity of said defect includes interdiffusing a plurality of said layer boundaries.

23. The method of claim 20, wherein the step of interdiffusing at least one layer boundary includes controlling the multilayer contraction associated with the densification that occurs upon interdiffusion at said at least one layer boundary.

24. The method of claim 23, wherein the step of controlling the multilayer contraction includes activating the step of interdiffusing using a localized energy source.

25. The method of claim 24, wherein said localized energy source comprises an electron beam.

26. The method of claim 25, wherein said electron beam is focused.

27. The method of claim 24, wherein said localized energy source is selected from the group consisting of an electromagnetic beam, an electron beam and an ion beam.

28. The method of claim 27, wherein said localized energy source is focused.

29. The method of claim 27, further comprising controlling the decrease in thickness of said multilayer coating by adjusting the energy dose of said localized energy source.

30. The method of claim 27, further comprising adjusting the energy dose of said localized energy source to control the decrease in film thickness with sub-nanometer accuracy.

31. The method of claim 27, further comprising controlling the lateral spatial resolution of the localization of energy deposition produced by said localized energy source.

32. The method of claim 27, wherein the depth of the deformation is controlled by adjusting the exposure time of said localized energy source.

33. The method of claim 23, wherein said densification comprises silicide formation.

34. The method of claim 24, wherein said localized energy source comprises an electrode.

35. The method of claim 19, wherein said defect comprises a mound or protrusion caused by multilayer deposition over a particle, wherein said defect is mitigated by decreasing the multilayer film thickness at the position of said defect, or spreading the sides of said mound, thereby reducing the slopes of said defect.

36. The method of claim 19, wherein said defect comprises a depression caused by multilayer deposition over a pit or scratch, wherein said defect is mitigated by increasing the multilayer film thickness at the position of the said defect, or spreading the sides of said depression, thereby reducing the slopes of said defect.

37. The method of claim 19, wherein said thin film coating comprises a reflective multilayer structure.

38. The method of claim 19, wherein said multilayer coating is used as a buffer layer, wherein said EUVL reticle further comprises a reflective multilayer coating deposited on said multilayer coating.

39. The method of claim 19, wherein said multilayer coating comprises Mo/Si.

40. The method of claim 1, wherein said sample comprises a multilayer coating wherein said defect comprises an amplitude defect in said multilayer coating, wherein said defect is selected from the group consisting of a particle, a shallow pit and a scratch, wherein the step for repairing said defect comprises removing said defect that is causing said amplitude defect from said multilayer coating, wherein a damaged region of said multilayer coating will remain after removal of said defect, wherein said step for repairing said defect further comprises etching away said damaged region.

41. The method of claim 40, wherein the step of etching away said damaged region is carried out without disturbing the intact underlying layers of said multilayer coating.

42. The method of claim 40, wherein the step of removing a particle includes milling said particle out of said multilayer coating.

43. The method of claim 42, wherein the step of milling is carried out with a focused ion beam (FIB).

44. The method of claim 43, wherein said FIB is operated near normal incidence.

45. The method of claim 43, wherein said FIB has a diameter less than 100 nm.

46. The method of claim 43, wherein said FIB comprises a gas source.

47. The method of claim 46, wherein said gas source comprises a gas selected from the group consisting of He, Ne, Ar, Xe, F, Cl, I and Br.

48. The method of claim 43, wherein said FIB comprises a liquid metal source.

49. The method of claim 48, wherein said liquid metal source comprises a liquid metal selected from the group consisting of Ga, Si, In, Pb and Hg.

50. The method of claim 43, further comprising imaging said defect with said FIB.

51. The method of claim 42, further comprising removing atoms implanted by milling step to remove defect.

52. The method of claim 40, further comprising imaging said defect during the step of removing and the step of etching.

53. The method of claim 52, wherein the step of imaging is carried out using a focused ion beam.

54. The method of claim 40, wherein the step of etching away said damaged region is carried out using an ion beam having a voltage of less than 5000 V.

55. The method of claim 54, wherein said ion beam has a diameter within the range from about 10 mn to about 1 mm.

56. The method of claim 54, wherein said ion beam is rotated with respect to said multilayer coating to improve the uniformity of the etching process.

57. The method of claim 40, wherein the step of etching away said damaged region is carried out at a temperature less than 200° C.

58. The method of claim 40, wherein the step of etching away said damaged region produces a crater in the surface of said multilayer coating that has a diameter of greater than 10 μm and a depth of less than 150 nm.

59. The method of claim 40, wherein the step of etching away said damaged region is carried out using an ion beam at an angle of incidence that is less than 20 degrees from the surface of said multilayer coating.

60. The method of claim 59, wherein said ion beam is rotated with respect to said multilayer coating to improve the uniformity of the etching process.

61. The method of claim 40, wherein said particle is on the top of, or imbedded near the surface of, said multilayer coating, surrounded by a localized region of damaged multilayer coating.

62. The method of claim 40, further comprising minimizing the slope of the surface of said multilayer coating in the repaired region.

63. The method of claim 40, further comprising depositing a Si layer subsequent to the step of removing a defect, wherein said Si layer is about 1 to 4 nm thick, wherein said Si layer limits oxidation of the exposed multilayer coating.

64. The method of claim 51, wherein the step of repairing said defect is carried out with an Atomic Force Microscope (AFM) having the capability to produce a crater.

65. The method of claim 1, wherein said defect comprises an amplitude defect in a multilayer coating, wherein the step of repairing said defect comprises physically removing said defect from said multilayer coating and leaving a wide, shallow crater that exposes the underlying intact layers to restore the local reflectivity of the coating.

* * * * *